(12) United States Patent
Li et al.

(10) Patent No.: US 8,742,085 B2
(45) Date of Patent: Jun. 3, 2014

(54) METHOD FOR PREPARING A TRANSGENIC ANIMAL OF SIMULTANEOUS MULTIPLE-GENE EXPRESSION

(75) Inventors: Kui Li, Beijing (CN); Huiming Ju, Yangzhou (CN); Junhua Fan, Beijing (CN); Lijing Bai, Beijing (CN); Yulian Mu, Beijing (CN); Shulin Yang, Beijing (CN); Zhonglin Tang, Beijing (CN); Wentao Cui, Beijing (CN)

(73) Assignee: Institute of Animal Science, Chinese Academy of Agricultural Sciences, Beijing (CN)

( * ) Notice: Subject to any disclaimer, the term of this patent is extended or adjusted under 35 U.S.C. 154(b) by 0 days.

(21) Appl. No.: 13/122,399

(22) PCT Filed: Jun. 24, 2010

(86) PCT No.: PCT/CN2010/000943
§ 371 (c)(1),
(2), (4) Date: Jun. 4, 2012

(87) PCT Pub. No.: WO2011/085528
PCT Pub. Date: Jul. 21, 2011

(65) Prior Publication Data
US 2012/0233717 A1    Sep. 13, 2012

(30) Foreign Application Priority Data

Jan. 15, 2010 (CN) .......................... 2010 1 0034318

(51) Int. Cl.
*C07H 21/04* (2006.01)
*C12N 15/00* (2006.01)
*A01K 67/027* (2006.01)

(52) U.S. Cl.
USPC .......... 536/23.2; 800/25; 435/455; 435/320.1

(58) Field of Classification Search
USPC ........................................... 536/23.2; 800/25
See application file for complete search history.

(56) References Cited

U.S. PATENT DOCUMENTS

| 5,625,123 | A  | * | 4/1997 | Shiho et al. ................. 800/3 |
| 6,695,767 | B2 | * | 2/2004 | Martinez Garcia et al. .... 600/35 |
| 7,115,795 | B1 | * | 10/2006 | Forsberg et al. .............. 800/14 |
| 2006/0200869 | A1 | * | 9/2006 | Naldini et al. ................. 800/14 |
| 2010/0154070 | A1 | * | 6/2010 | Xu et al. ....................... 800/13 |

FOREIGN PATENT DOCUMENTS

| WO | WO 87/00864 | * | 2/1987 |
| WO | WO 2006/037052 | * | 4/2006 |
| WO | WO 2006/063588 | * | 6/2006 |

OTHER PUBLICATIONS

Pavlovic et al. Enhanced virus resistance of transgenic mice expressing the human MxA protein. J. Virol. 69:4506-4510, 1995.*

* cited by examiner

*Primary Examiner* — Quang Nguyen
(74) *Attorney, Agent, or Firm* — Knobbe, Martens, Olson & Bear, LLP

(57) ABSTRACT

A method for preparing a transgenic animal of simultaneous multiple-gene expression is provided. Additionally, a method for preparing a transgenic embryo, which introduces both phytase gene and human myxovirus resistant gene A into a target embryo, to obtain a transgenic embryo is provided. The transgenic animal of simultaneous multiple-gene expression can be achieved by transplanting the transgenic embryo into the body of a female target animal. A significant advantage of the foregoing methods, among many others, exists in that the simultaneous expression of multiple genes can be achieved in one transgenosis, which provides a convenient method for the preparation of combined-gene transferred animals.

4 Claims, 5 Drawing Sheets

METHOD FOR PREPARING A TRANSGENIC ANIMAL OF SIMULTANEOUS MULTIPLE-GENE EXPRESSION

CROSS-REFERENCE TO RELATED APPLICATION

This application is U.S. National Phase of International Application No. PCT/CN2010/000943, filed Jun. 24, 2010, designating the United States, which claims the benefit of Chinese Application No. 201010034318.3, filed Jan. 15, 2010. The International Application was filed in Chinese and has not been published as of the filing date of the present U.S. National Phase application. The Chinese language application and its associated documents as originally filed in the International Application are hereby incorporated in their entirety.

REFERENCE TO SEQUENCE LISTING

The present application incorporates by reference the sequence listing submitted as an ASCII text filed via EFS-Web on Jan. 29, 2014. The Sequence Listing is provided as a file entitled 17132097 1.txt, created on Jan. 28, 2014, which is 11.1 Kb in size.

TECHNICAL FIELD

The present invention relates to the field of biotechnology, especially relates to a method for preparing a transgenic animal of simultaneous multiple-gene expression.

BACKGROUND OF THE INVENTION

In the research of traditional preparation of transgenic animals, the research is usually achieved by means of eukaryotic expression vectors. After a target gene fragment is linked downstream of a eukaryotic promoter and is integrated into a cellular genome by molecular biological means, the expression of the exogenous gene can be directed. The method is broadly used in the research of genetic expression and function. Traditional transgenic methods only integrate one target gene per transgenosis, and thereby prepare a transgenic animal expressing one gene. In case that the preparation of a transgenic animal of multiple genes is concerned, it needs to prepare corresponding transgenic animals of single gene separately, and then prepare the progenies of multiple transgenic animals by the method of mating between transgenic animals and the like. Such method for preparing polygenic animals takes time and work, and costs much.

DISCLOSURE OF THE INVENTION

The object of the present invention is to provide a method for preparing a transgenic embryo.

In the method for preparing a transgenic embryo provided in the invention, both of phytase gene and human myxovirus resistant gene A are introduced into a target embryo to obtain a transgenic embryo.

The nucleotide sequence of aforementioned phytase gene is presented as positions 1360-2658 from 5'-terminal of SEQ ID NO. 1 in the Sequence Listing. The nucleotide sequence of aforementioned human myxovirus resistant gene A is presented as positions 3803-5791 from 5'-terminal of SEQ ID NO. 1 in the Sequence Listing.

Specifically, aforementioned phytase gene and human myxovirus resistant gene A can be introduced into the embryo by a DNA fragment with nucleotide to sequence presented as SEQ ID NO. 1 in the Sequence Listing.

Aforementioned embryo is an embryo in pronuclear stage. Aforementioned embryo is an embryo of any animal except human, which may specifically be an embryo of pig, cattle, sheep, cat, dog, rabbit or murine.

Another purpose of the present invention exists in provision of a method for cultivating a transgenic animal.

In the method for cultivating a transgenic animal provided in the present invention, the transgenic embryo prepared by the aforementioned method for preparing a transgenic embryo is transplanted into the body of a female target animal to obtain a transgenic animal capable of expressing multiple genes simultaneously.

Aforementioned target animal can be any animal except human, which may specifically be a pig, cattle, sheep, cat, dog, rabbit or murine.

DESCRIPTION OF THE DRAWINGS

FIG. 5: The profile of plasmid pcDNA-appA-MxA.

PREFERRED EMBODIMENTS FOR CARRYING OUT THE INVENTION

Hereinafter, the present invention will be further described in combination with specific examples. However, the present invention is not limited to the following examples.

In the following examples, conventional methods are used, unless indicated otherwise.

EXAMPLE 1

Preparation of Transgenic Embryos

I. Construction of Recombinant Expression Vectors

Example 1

Construction of Vectors of Two-Gene Expression

Figure 1:
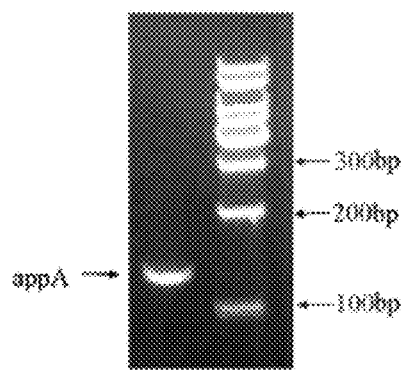
FIG. 1: The gel electrophoresis image of amplified appA.

1. Obtainment of Basic Components of a Single-Gene Expression Vector
(1) Preparation of Eukaryotic Expression Vector pcDNA-appA Using *Escherichia coli* DH5α (commercially available from Beijing TransGen Biotech Co. Ltd., Catalog No. CD201) as template, the fragments of phytase gene (appA) are amplified with the primers for appA amplification listed in Table 1. The reaction system is 50 μL, which contains 5 μL of 10× Buffer, 8 μL of 2.5 mM dNTP, 1 μL of 20 μM primer appA-L1, 1 μL of 20 μM primer appA-R1 (see Table 1 for the sequences of the primers), 0.5 μL of 5 U/μL high-fidelity Taq polymerase, and 2 μl of *Escherichia coli* DH5α as template, added up to 50 μL with ultra-pure water (the high-fidelity enzyme is commercially available from Takara Biotechnology (Dalian) Co. Ltd., Catalog No. DR010A). The procedure of PCR amplification: 98L for 10 s and 68° C. for 2 min, 30 cycles. The PCR amplified products are detected with 1% agarose gel electrophoresis (as shown in FIG. 1).

Figure 2:
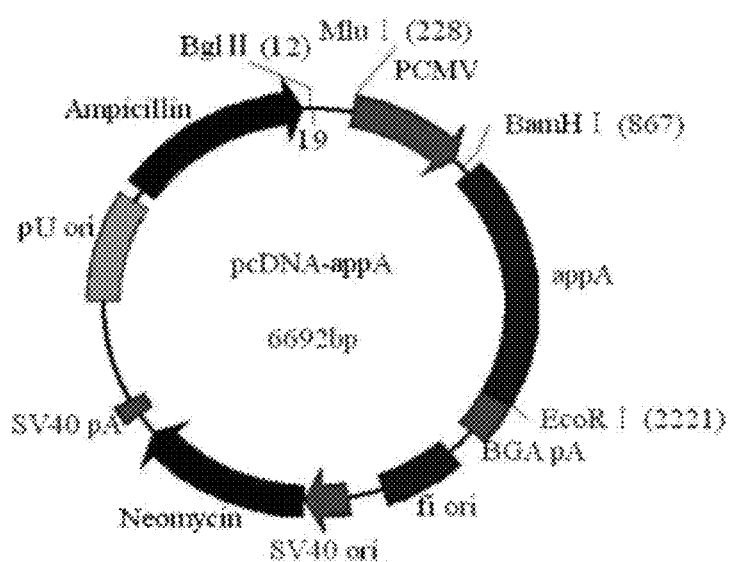
FIG. 2: The profile of plasmid pcDNA-appA.

The PCR products are recovered and purified using QIAGEN agarose gel kit (see the kit for the operating steps), and the products purified are cut by two enzymes of HindIII and EcoR I. Meanwhile, pcDNA3.1(+) vectors (commercially available from Invitrogen Corporation) are cut by two enzymes of HindIII and EcoR I. The PCR amplified products and cleaved vectors are linked (the ligase is commercially available from Promega Corporation, Catalog No. M1804). The competent *Escherichia coli* DH5α (commercially available from Beijing TransGen Biotech Co., Ltd., Catalog No. CD201) is transformed according to the operating steps required by the manufacture. The DH5α liquid is coated onto an agarose gel plate, and cultivated at 37° C. in an incubator overnight. A single colony is picked and inoculated into a liquid LB medium for culture, and part of the DH5α liquid is sent to Invitrogen Beijing Office for sequencing. The vectors in which appA (the nucleotide sequence is presented as positions 1360-2658 from 5'-terminal of SEQ ID NO. 1 in the Sequence Listing) is demonstrated to be contained by sequencing results are selected, and the plasmids are extracted for use. The plasmid demonstrated to be correct by sequencing is named as plasmid pcDNA-appA (the profile of the plasmid is shown in FIG. 2).

(2) Preparation of Eukaryotic Expression Vector pcDNA-MxA

Figure 3:
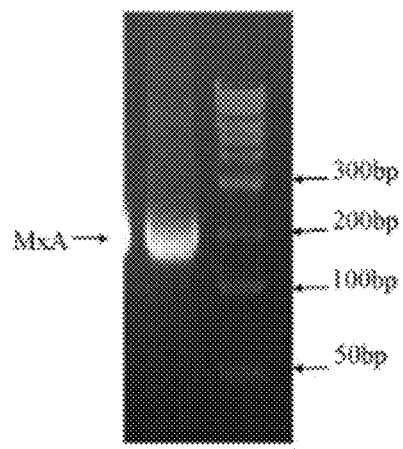
FIG. 3: The gel electrophoresis image of amplified MxA.

Using human cDNA (obtained from the extraction of total RNA from the human blood ex vivo, and reverse transcription) as template, the fragments of human myxovirus resistant gene A (MxA) are amplified with the primers for MxA amplification listed in Table 1. The reaction system is 50 μL, containing 5 μL of 10× Buffer, 8 μL of 2.5 mM dNTP, 1 μL of 20 μM primer Mx-L1, 1 μL of 20 μM primer Mx-R1 (see Table 1 for the sequences), 0.5 μL of 5 U/μL high-fidelity Taq polymerase, and 100 ng of human cDNA as template, added up to 50 μL with ultra-pure water (the high-fidelity enzyme is commercially available from Takara Biotechnology (Dalian) Co. Ltd., Catalog No. DR010A). The procedure of PCR amplification: 98° C. for 10 s and 68° C. for 2 min, 30 cycles. The PCR amplified products are detected with 1% agarose gel electrophoresis (FIG. 3).

Figure 4:
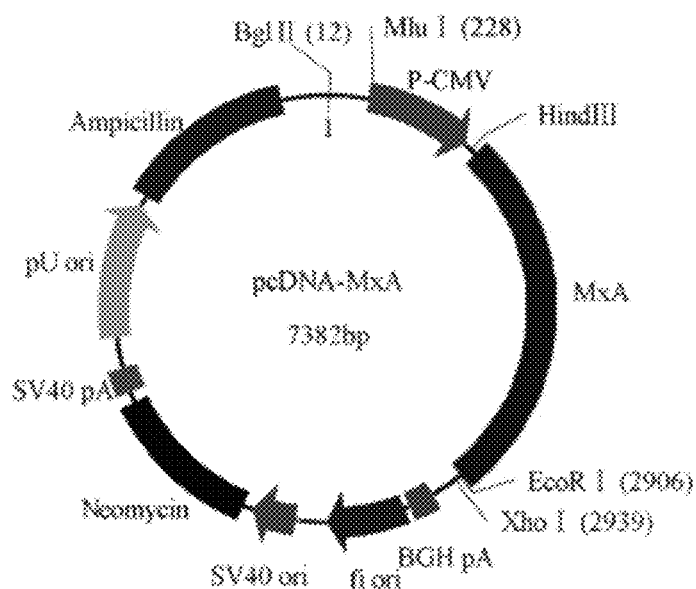
FIG. 4: The profile of plasmid pcDNA-MxA.
Figure 3:
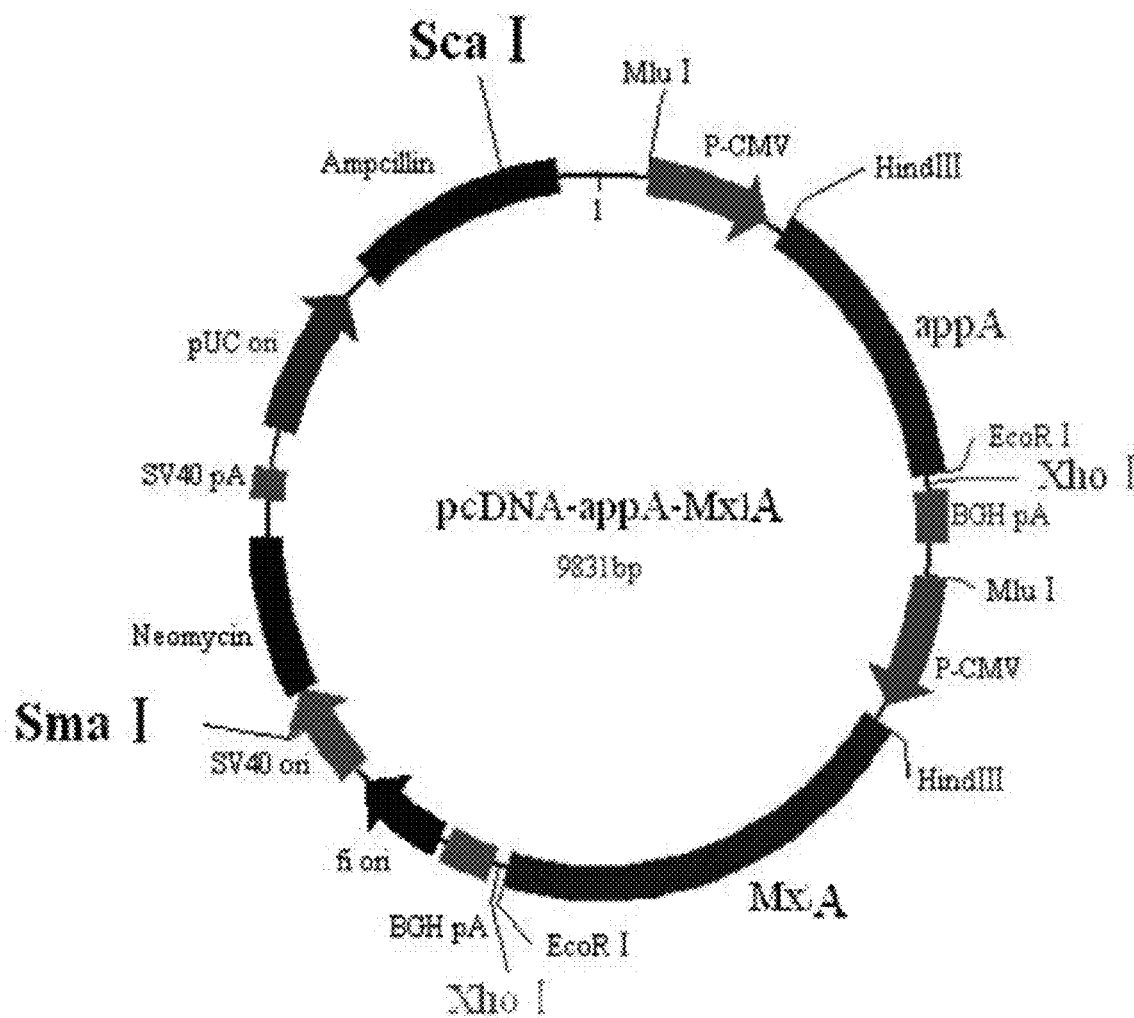

The PCR products are recovered and purified using QIAGEN agarose gel kit (see the kit for the operating steps), and the products purified are cut by two enzymes of HindIII and EcoR I. Meanwhile, pcDNA3.1(+) vectors (commercially available from Invitrogen Corporation) are cut by two enzymes of HindIII and EcoR I. The PCR amplified products and cleaved vectors are linked (the ligase is commercially available from Promega Corporation, Catalog No. M1804). The competent *Escherichia coli* DH5α (commercially available from Beijing TransGen Biotech Co., Ltd., Catalog No. CD201) is transformed according to the operating steps required by the manufacture. The DH5α liquid is coated onto an agarose gel plate, and cultivated at 37° C. in an incubator overnight. A single colony is picked and inoculated into a liquid LB medium for culture, and part of the DH5α liquid is sent to Invitrogen Beijing Office for sequencing. The vectors in which MxA fragment (the nucleotide sequence is presented as positions 3803-5791 from 5'-terminal of SEQ ID NO. 1 in the Sequence Listing) is demonstrated to be contained by sequencing results are selected, and the plasmids are extracted for use. The plasmid demonstrated to be correct by sequencing is named as plasmid pcDNA-MxA (the profile of the plasmid is shown in FIG. 4).

2. Construction of Two-Gene Expression Vectors, AMP

Using aforementioned pcDNA-appA (the profile of the plasmid is shown as in FIG. 2) as template, the corresponding components as listed in Table 1 are amplified with the primers listed in Table 1. 5 μL of 10× Buffer, 8 μL of 2.5 mM dNTP, 1 μL of 20 μM primer CMV-appA-L1, 1 μL of 20 μM primer CMVappA-R1 (see Table 1 for the sequences), 0.5 μL of 5 U/μL high-fidelity Taq polymerase, and 100 ng of plasmid pcDNA-appA, are added up to 50 μL with ultra-pure water (the high-fidelity enzyme is commercially available from Takara Biotechnology (Dalian) Co. Ltd., Catalog No. DR010A). The procedure of PCR amplification: 98° C. for 10 s and 68° C. for 3 min, 30 cycles. The PCR amplified products are detected with 1% agarose gel electrophoresis. Part of the PCR products are sequenced (Invitrogen Corporation), demonstrating that fragment CMV-appA-BGH pA (the nucleotide sequence is presented as positions 618-2977 from 5'-terminal of SEQ ID NO. 1 in the Sequence Listing) is obtained from amplification. The fragment CMV-appA-BGH pA is comprised of promoter CMV, appA and terminator BGH concatenated in turn; with promoter CMV (the nucleotide sequence is presented as positions 671-1358 from 5'-terminal of SEQ ID NO. 1 in the Sequence Listing), appA (the nucleotide sequence is presented as positions 1360-2658 from 5'-terminal of SEQ ID NO. 1 in the Sequence Listing) and terminator BGH (the nucleotide sequence is presented as positions 2735-2959 from 5'-terminal of SEQ ID NO. 1 in the Sequence Listing).

Aforementioned PCR products of CMV-appA-BGH pA fragment are recovered and purified with QIAGEN agarose gel kit (see the kit for the operating steps), and the products purified are cut by Mlu I enzyme. Meanwhile, plasmid pcDNA-MxA is cut with single enzyme of Mlu I. The PCR amplified products and cleaved vectors are linked (the ligase is commercially available from Promega Corporation, Catalog No. M1804). The competent *Escherichia coli* DH5α (commercially available from Beijing TransGen Biotech Co., Ltd., Catalog No. CD201) is transformed according to the operating steps required by the manufacture. The DH5α liquid is coated onto an agarose gel plate, and cultivated at 37° C. in an incubator overnight.

A single colony is picked and inoculated into a liquid LB medium for culture. PCR is used to detect fragment CMV-appA-BGH pA in inserted fragment for DH5α liquid (the amplification system is the same as above part of the amplification of fragment CMV-appA-BGH pA (the primers are seen in Table 1), wherein the template is changed to be 2 μL of DH5α liquid). As a result, there presents corresponding amplified band of fragment CMV-appA-BGH pA. Parts of the DH5α liquid of both samples described above are sent to Invitrogen Beijing Office for sequencing. The result shows that the recombinant expression vectors containing fragment CMV-appA-BGH pA and expression cassette MxA are obtained. Such vector is named as pcDNA-appA-MxA, abbreviated to AMP. The profile of plasmid of AMP is shown as FIG. 5.

The sequencing shows that AMP has the nucleotide sequence of SEQ ID NO. 1 in the Sequence Listing, which sequence contains expression cassettes of appA and MxA.

Wherein, expression cassette appA is comprised of promoter CMV (the nucleotide sequence is presented as positions 671-1358 from 5'-terminal of SEQ ID NO. 1 in the Sequence Listing), appA (the nucleotide sequence is presented as positions 1360-2658 from 5'-terminal of SEQ ID NO. 1 in the Sequence Listing) and terminator BGH (the nucleotide sequence is presented as positions 2735-2959 from 5'-terminal of SEQ ID NO. 1 in the Sequence Listing) concatenated in turn; expression cassette MxA is comprised of promoter CMV (the nucleotide sequence is presented as positions 3114-3802 from 5'-terminal of SEQ ID NO. 1 in the Sequence Listing), MxA (the nucleotide sequence is presented as positions 3803-5791 from 5'-terminal of SEQ ID NO. 1 in the Sequence Listing) and terminator BGH (the nucleotide sequence is presented as positions 5868-6092 from 5'-terminal of SEQ ID NO. 1 in the Sequence Listing) concatenated in turn.

II. Preparation of Transgenic Embryos

1. The pcDNA-appA-MxA obtained from Step I is cut by two enzymes of ScaI (commercially available from Fermentas Corporation, Catalog No. ER0431) and SmaI (commercially available from Fermentas Corporation, Catalog No. ER0661). Then, agarose gel electrophoresis is used to recover the band of 6.9 Kb size, which is diluted to 5 ng/μL. The sequencing shows that the nucleotide sequence of the band of 6.9 Kb is presented as of SEQ ID NO. 1 in the Sequence Listing.

The linearized fragment of 6.9 Kb described above is injected into a porcine embryo in pronuclear stage using microinjection method to obtain the transgenic embryo, and cultivated in NCSU 23 medium (commercially available from Millipore Corporation, Catalog No. MR-182-D) to 8 cell stage.

2. Detection for the Transgenic Embryos

Figure 6:
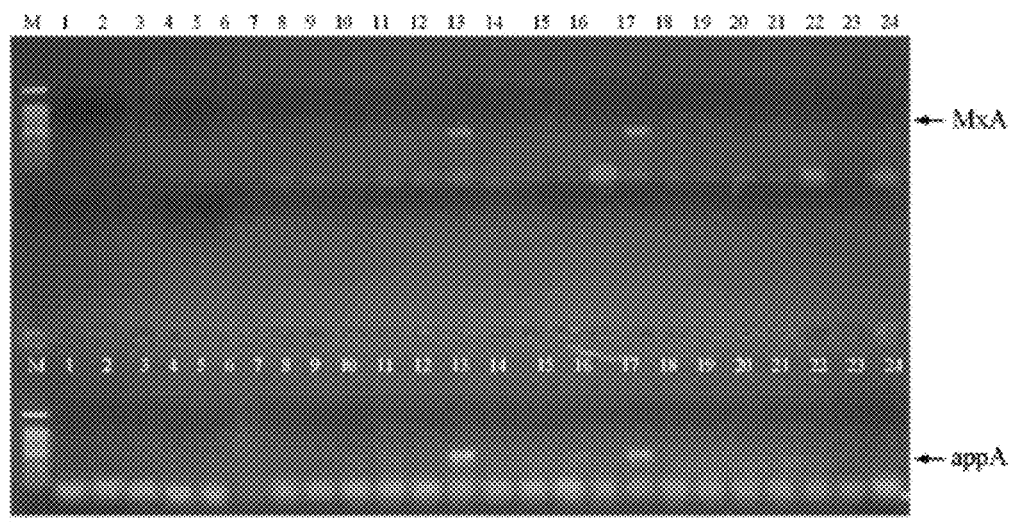
FIG. 6: The quantitative detection for the expression of appA and MxA in embryo after the microinjection of AMP gene.

Genomic DNA of part of the embryos is taken as template directly, and according to the operating instruction of ProtoScript M-MuLV Taq RT-PCR Kit (commercially available from NEB Corporation, Catalog No. E6400S) (the primers are the primers for quantitative PCR detection of appA and MxA as listed in Table 1), appA (the primers are appA-RTL1 and appA-RTR1 in Table 1) and MxA (the primers are hMx1-RTL1 and hMx1-RTR1 in Table 1) in embryos are directly detected. The reaction system of PCR is 50 μL, which contains 5 μL of 10× Buffer, 8 μL of 2.5 mM dNTP, 1 μL of 20 μM upstream primer, 1 μL of 20 μM downstream primer, 0.5 μL of 5 U/μL high-fidelity Taq polymerase, added up to 50 μL with ultra-pure water. The genomic DNA of small pigs obtained are used as template to be detected. The procedure of PCR amplification: 95° C. for 5 min; 94° C. for 20 s, annealing temperature of 56° C. and 72° C. for 1 min, 30 cycles, and finally extension at 72° C. for 5 min. The PCR amplified products are detected with 1.0% agarose gel electrophoresis, screening out the embryos in which genes appA and MxA may be amplified, respectively. The result shows that, among the 24 embryos detected, Nos. 13 and 17 of the embryos are detected to have the capacity of simultaneous expression of appA gene and MxA gene (FIG. 6).

EXAMPLE 2

Preparation of Transgenic Animals

I. Preparation of Transgenic Animals

The transgenic embryos prepared by the method of Example 1 are developed to 8 cell stage in vitro, and transplanted into the uterine horns of estrus synchronized sow through vaginal cervix in vitro. After cultivation, 38 transgenic pigs are obtained.

II. Integration Detection for Transgenic Pigs

1. PCR Detection

Using the primers for appA and MxA quantitative detection (see Table 1), the integration of corresponding genes in the genomic DNA of transgenic pigs and the integration condition of the exogenous genes in above transgenic pigs are detected.

The PCR reaction system and amplification system are the same as those of detection of the transgenic embryo in Step II of Example 1, screening out the pigs in which genes appA and MxA can be amplified respectively (FIG. 7) (in the figure, +: positive control, with plasmid pcDNA-appA-Mx as template; −: negative control, with DNA of normal pigs as template; 1-23: amplified bands of different transgenic porcine progenies).

Figure 7:
FIG. 7: The PCR detection for the exogenous gene of AMP transgenic pigs.

As can be seen from upper part of FIG. 7, among the pigs of Nos. 1-23, the genomic DNA from the pigs of Nos. 3, 6, 11, 17, 20 and 22 may be amplified to obtain the band of about 355 bp, which is consistent with the expected appA amplification band. As can be seen from the lower part of FIG. 7, among the pigs of Nos. 1-23, the genomic DNA of pigs of Nos. 3, 6, 11, 17, 20 and 22 may be amplified to obtain the band of 325 bp, which is consistent with the expected MxA amplification band. The sequencing for amplified products indicates that the nucleotide sequences of the amplified fragments are all correct.

2, Southern Hybridization Detection

Using the primers for quantitative PCR detection of appA and MxA in Table 1 as primers respectively, the system is loaded according to the operating instruction of the kit. PCR processing procedure is as follows: 95° C. for 5 min, 94° C. for 45 s, 56° C. for 1 min and 72° C. for 1 min, 30 cycles, and subsequent extension at 72° C. for 10 min (the probe labeling kit is commercially available from Innogen-cn Corporation, Catalog No. DDLK-010), to obtain two PCR products.

Figure 8:
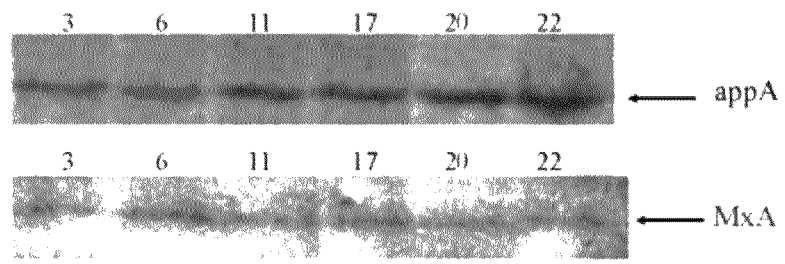
FIG. 8: The SOUTHERN BLOT detection for the exogenous gene of AMP transgenic pigs.

The southern hybridization detection is performed using the aforementioned two PCR products as probe respectively. Before the hybridization, the PCR products are denatured at 95° C. for 5 minutes and then immediately placed into ice water for 10 minutes for use. The DNAs of the porcine auricular tissues of the transgenic pigs numbered as Nos. 3, 6, 11, 17, 20 and 22 as identified in Step 1 are extracted in large amount, and the genomes are cut by two enzymes of Hind III and Not I and the cleaved products of the genomes are concentrated to 300 ng/μl. The cleaved fragments are separated by 1% agarose gel electrophoresis, with the loading amount of 50 μL per well. Then DNAs are denatured in situ, and subsequently transferred onto a nylon film charged positively. According to the operating instruction of the kit, pre-hybridization, hybridization and X-ray film exposure for detecting hybridization signals (commercially available from Innogen-cn Corporation, Catalog No. DIGD-210) are performed. The result of detection (FIG. 8) shows that genes appA and MxA are integrated into the transgenic pigs numbered as Nos. 3, 6, 11, 17, 20 and 22 in southern hybridization detection.

III. RT-PCR Detection

100 μL of blood is collected from the porcine auricular veins of the transgenic pigs numbered as Nos. 3, 6, 11, 17, 20 and 22 screened out in Step II, from which the total RNA of each group of cells is extracted according to the operating instruction of Tiangen Blood Total RNA Extraction Kit (Catalog No. DP433). The total RNA extracted is reverse transcribed to cDNA according to TOYOBO Reverse Transcription Kit (Catalog No. FSK-100).

Using aforementioned cDNAs as template respectively, the semi-quantitative PCR detection of appA and MxA is conducted with the primers for quantitative PCR detection of appA and MxA in Table 1, wherein porcine GAPDH gene is used as internal reference (see Table 1 for the primers). The reaction system of PCR is 50 μL, which contains 5 μL of 10× Buffer, 8 μL of 2.5 mM dNTP, 1 μL of 20 μM upstream primer, 1 μL of 20 μM downstream primer (the primers used to amplify appA, MxA and porcine GAPDH are seen in Table 1, respectively), 0.5 μL of 5 U/μL high-fidelity Taq polymerase and 100 ng of template, added up to 50 μL with ultra-pure water.

The procedure of PCR amplification: 95° C. for 5 min; 94° C. for 20 s, annealing temperature of 56° C. and 72° C. for 1 min, and finally extension at 72° C. for 5 min, 23 cycles for amplification of internal reference GAPDH and 32 cycles for amplification of other templates.

Figure 9:
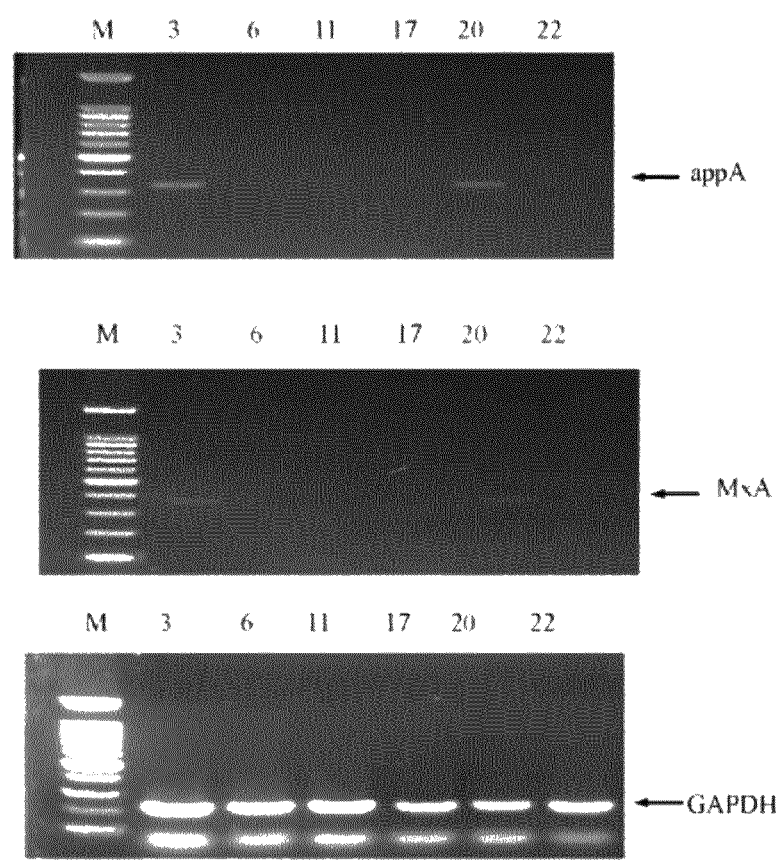
FIG. 9: The quantitative detection for the expression of appA and MxA.

The PCR amplified products are detected using 1.2% agarose gel electrophoresis (FIG. 9). The semi-quantitative result shows that the expression of MxA and appA can be found in both pigs of Nos. 3 and 20, indicating that both of genes MxA and appA can be simultaneously expressed in the corresponding transgenic pigs.

TABLE 1

Primers used for amplifying vector components in the present invention

| Name of amplified fragment | Primer symbol | Primer sequence | Product length | Cleavage site introduced at 5'-terminal |
|---|---|---|---|---|
| Fragment of Phytase (appA) | appA-L1 | CGC<u>AAGCTT</u>ATGAAAGCGATC TTAATCCCA (SEQ ID NO: 2) | 1299 | HindIII (underlined) |
| | appA-R1 | CAC<u>GAATTC</u>TTACAAACTGCA CGCCGGTATG (SEQ ID NO: 3) | | EcoRI (underlined) |
| MxA fragment | Mx-L1 | AGC<u>AAGCTT</u>ATGGTTGTTTCC GAAGTGG (SEQ ID NO: 4) | 1989 | HindIII (underlined) |
| | Mx-R1 | TAT<u>GAATTC</u>CTAACCGGGGAA CTGGGCA (SEQ ID NO: 5) | | EcoR I |
| CMV-appA-BGH pA fragment | CMVappA-L1 | ATCTGCTTAGGGTTAGGCGTT TTGC (SEQ ID NO: 6) | 2358 | |
| | CMVappA-R1 | ata<u>ACGCGT</u>TTCTTTCCGCCTC AGAAGCC (SEQ ID NO: 7) | | MluI (underlined) |
| quantitative PCR detection of appA | appA-RTL1 | CGTGAGAAACAGGACGAAAG (SEQ ID NO: 8) | 355 | — |
| | appA-RTR1 | GCCGAGATTTGCCAGATTAG (SEQ ID NO: 9) | | — |
| quantitative PCR detection of Mx1 | hMx1-RTL1 | GCATCCCACCCTCTATTAC (SEQ ID NO: 10) | 325 | — |
| | hMx1-RTR1 | CCTTGCCTCTCCACTTATC (SEQ ID NO: 11) | | — |
| quantitative PCR detection of Pig GAPDH as internal reference | mGAPDH-L1 | TACACAGCCACTCAGAAGAC (SEQ ID NO: 12) | 249 | — |
| | mGAPDH-R1 | TTTCACAGCCTCCGTGATAG (SEQ ID NO: 13) | | — |

INDUSTRIAL APPLICATION

The present invention prepares transgenic pig containing two genes (phytase gene (appA) and human myxovirus resistant gene A (MxA)) by using eukaryotic expression vector of spcDNA-appA-MxA expressing simultaneously phytase gene and human myxovirus resistant gene while construction, and using microinjection method. With the capacity of detection of transgenic pig and integration of two genes simultaneously, the significant advantage of the vector of the invention exists in that the simultaneous expression of multiple genes can be achieved in one transgenosis, which provides a convenient mean for the preparation of combined-gene transferred animals.

---

What is claimed is:

1. A nucleotide molecule comprising the sequence of SEQ ID NO: 1.

2. A method for preparing a transgenic porcine embryo, the method comprising:

introducing the nucleotide molecule of claim 1 into a target porcine embryo so as to obtain a transgenic porcine embryo, said nucleotide molecule comprising phytase gene and human myxovirus resistant gene A.

3. The method according to claim 2, wherein the target porcine embryo is a porcine embryo in pronuclear stage.

4. A method for cultivating a transgenic pig, the method comprising:

transplanting the transgenic porcine embryo prepared by the method of claim 2 into uterine horns of estrus synchronized sow through vaginal cervix so as to obtain the transgenic pig, wherein said transgenic pig is capable of simultaneously expressing multiple genes.

* * * * *

SEQUENCE LISTING

```
<160> NUMBER OF SEQ ID NOS: 13

<210> SEQ ID NO 1
<211> LENGTH: 6915
<212> TYPE: DNA
<213> ORGANISM: Artificial sequence
<220> FEATURE:
<223> OTHER INFORMATION: Synthetic oligonucleotide

<400> SEQUENCE: 1
actcaaccaa gtcattctga gaatagtgta tgcggcgacc gagttgctct tgcccggcgt     60
caatacggga taataccgcg ccacatagca gaactttaaa agtgctcatc attggaaaac    120
gttcttcggg gcgaaaactc tcaaggatct taccgctgtt gagatccagt tcgatgtaac    180
ccactcgtgc acccaactga tcttcagcat cttttacttt caccagcgtt tctgggtgag    240
caaaaacagg aaggcaaaat gccgcaaaaa agggaataag ggcgacacgg aaatgttgaa    300
tactcatact cttcctttt caatattatt gaagcattta tcagggttat tgtctcatga    360
gcggatacat atttgaatgt atttagaaaa ataaacaaat aggggttccg cgcacatttc    420
cccgaaaagt gccacctgac gtcgacggat cgggagatct cccgatcccc tatggtgcac    480
```

```
tctcagtaca atctgctctg atgccgcata gttaagccag tatctgctcc ctgcttgtgt    540
gttggaggtc gctgagtagt gcgcgagcaa aatttaagct acaacaaggc aaggcttgac    600
cgacaattgc atgaagaatc tgcttagggt taggcgtttt gcgctgcttc gcgatgtacg    660
ggccagatat acgcgttgac attgattatt gactagttat taatagtaat caattacggg    720
gtcattagtt catagcccat atatggagtt ccgcgttaca taacttacgg taaatggccc    780
gcctggctga ccgcccaacg accccgccc attgacgtca ataatgacgt atgttcccat    840
agtaacgcca atagggactt tccattgacg tcaatgggtg gagtatttac ggtaaactgc    900
ccacttggca gtacatcaag tgtatcatat gccaagtacg ccccctattg acgtcaatga    960
cggtaaatgg cccgcctggc attatgccca gtacatgacc ttatgggact ttcctacttg   1020
gcagtacatc tacgtattag tcatcgctat taccatggtg atgcggtttt ggcagtacat   1080
caatgggcgt ggatagcggt ttgactcacg gggatttcca agtctccacc ccattgacgt   1140
caatgggagt ttgttttggc accaaaatca acgggacttt ccaaaatgtc gtaacaactc   1200
cgccccattg acgcaaatgg gcggtaggcg tgtacggtgg gaggtctata taagcagagc   1260
tctctggcta actagagaac ccactgctta ctggcttatc gaaattaata cgactcacta   1320
tagggagacc caagctggct agcgtttaaa cttaagctta tgaaagcgat cttaatccca   1380
tttttatctc ttctgattcc gttaaccccg caatctgcat tcgctcagag tgagccggag   1440
ctgaagctgg aaagtgtggt gattgtcagt cgtcatggtg tgcgtgctcc aaccaaggcc   1500
acgcaactga tgcaggatgt caccccagac gcatggccaa cctggccggt aaaactgggt   1560
tggctgacac cgcgcggtgg tgagctaatc gcctatctcg acattacca cgccagcgt    1620 ctggtagccg acggattgct ggcgaaaaag ggctgcccgc agtctggtca ggtcgcgatt   1680
attgctgatg tcgacgagcg tacccgtaaa acaggcgaag ccttcgccgc cgggctggca   1740
cctgactgtg caataaccgt acatacccag gcagatacgt ccagtcccga tccgttattt   1800
aatcctctaa aaactggcgt tgccaactg gataacgcga acgtgactga cgcgatcctc    1860
agcagggcag gagggtcaat tgctgacttt accgggcatc ggcaaacggc gtttcgcgaa   1920
ctggaacggg tgcttaattt tccgcaatca aacttgtgcc ttaaacgtga aaacaggac    1980 gaaagctgtt cattaacgca ggcattacca tcggaactca aggtgagcgc cgacaatgtc   2040
tcattaaccg gtgcggtaag cctcgcatca atgctgacga agatatttct cctgcaacaa   2100
gcacagggaa tgccggagcc ggggtgggga aggatcaccg attcacacca gtggaacacc   2160
ttgctaagtt tgcataacgc gcaatttat ttgttacaac gcacgccaga ggttgcccgc    2220
agccgcgcca ccccgttatt agatttgatc aagacagcgt tgacgcccca tccaccgcaa   2280
aaacaggcgt atggtgtgac attacccact tcagtgctgt ttatcgccgg acacgatact   2340
aatctggcaa atctcggcgg cgcactggag ctcaactgga cgcttcccgg tcagccggat   2400
aacacgccgc caggtggtga actggtgttt gaacgctggc gtcggctaag cgataacagc   2460
cagtggattc aggtttcgct ggtcttccag actttacagc agatgcgtga taaaacgccg   2520
ctgtcattaa atacgccgcc cggagaggtg aaactgaccc tggcaggatg tgaagagcga   2580
aatgcgcagg gcatgtgttc gttggcaggt tttacgcaaa tcgtgaatga agcacgcata   2640
ccggcgtgca gtttgtaaga attctgcaga tatccacac agtggcggcc gctcgagtct   2700
agagggcccg tttaaaccc ctgatcagcc tcgactgtgc cttctagttg ccagccatct    2760
gttgtttgcc cctcccccgt gccttccttg accctggaag gtgccactcc cactgtcctt   2820
tcctaataaa atgaggaaat tgcatcgcat tgtctgagta ggtgtcattc tattctgggg   2880
```

```
ggtggggtgg ggcaggacag caaggggag gattgggaag acaatagcag gcatgctggg    2940
gatgcggtgg gctctatggc ttctgaggcg gaaagaacca gctgggctc tagggggtat    3000 ccccacgcgc cctgtagcgg cgcattaagc gcggcgggtg tggtggttac gcgcagcgtg    3060
accgctacac ttgccagcgc cctagcgccc gctccttcg ctttcttccc ttcacgcgtt    3120
gacattgatt attgactagt tattaatagt aatcaattac ggggtcatta gttcatagcc    3180
catatatgga gttccgcgtt acataactta cggtaaatgg cccgcctggc tgaccgccca    3240
acgacccccg cccattgacg tcaataatga cgtatgttcc catagtaacg ccaatagggga   3300 ctttccattg acgtcaatgg gtggagtatt tacggtaaac tgcccacttg gcagtacatc    3360
aagtgtatca tatgccaagt acgccccta ttgacgtcaa tgacggtaaa tggcccgcct     3420
ggcattatgc ccagtacatg accttatggg actttcctac ttggcagtac atctacgtat    3480
tagtcatcgc tattaccatg gtgatgcggt tttggcagta catcaatggg cgtggatagc    3540
ggtttgactc acggggattt ccaagtctcc accccattga cgtcaatggg agtttgtttt    3600
ggcaccaaaa tcaacgggac tttccaaaat gtcgtaacaa ctccgcccca ttgacgcaaa    3660
tgggcggtag gcgtgtacgg tgggaggtct atataagcag agctctctgg ctaactagag    3720
aacccactgc ttactggctt atcgaaatta atacgactca ctatagggag acccaagctg    3780
gctagcgttt aaacttaagc ttatggttgt ttccgaagtg gacatcgcaa agctgatcc     3840 agctgctgca tcccacctc tattactgaa tggagatgct actgtggccc agaaaaatcc     3900
aggctcggtg gctgagaaca acctgtgcag ccagtatgag gagaaggtgc gcccctgcat    3960
cgacctcatt gactccctgc gggctctagg tgtggagcag gacctggccc tgccagccat    4020
cgccgtcatc ggggaccaga gctcgggcaa gagctccgtg ttggaggcac tgtcaggagt    4080
tgcccttccc agaggcagcg ggatcgtgac cagatgcccg ctggtgctga aactgaagaa    4140
acttgtgaac gaagataagt ggagaggcaa ggtcagttac caggactacg agattgagat    4200
ttcggatgct tcagaggtag aaaaggaaat taataaagcc cagaatgcca tcgccgggga    4260
aggaatggga atcagtcatg agctaatcac cctggagatc agctcccgag atgtcccgga    4320
tctgactcta atagaccttc ctggcataac cagagtggct gtgggcaatc agcctgctga    4380
cattgggtat aagatcaaga cactcatcaa gaagtacatc cagaggcagg agacaatcag    4440
cctggtggtg gtccccagta atgtggacat tgccaccaca gaggctctca gcatggccca    4500
ggaggtggac cccagggag acaggaccat cggaatcttg acgaagcctg atctggtgga    4560
caaaggaact gaagacaagg ttgtggacgt ggtgcggaac ctcgtgttcc acctgaagaa    4620
gggttacatg attgtcaagt gccgggggcca gcaggagatc caggaccagc tgagcctgtc    4680
cgaagccctg cagagagaga agatcttctt tgagaaccac ccatatttca gggatctgct    4740
ggaggaagga aaggccacgg ttccctgcct ggcagaaaaa cttaccagcg agctcatcac    4800
acatatctgt aaatctctgc ccctgttaga aaatcaaatc aaggagactc accagagaat    4860
aacagaggag ctacaaaagt atggtgtcga cataccggaa gacgaaaatg aaaaaatgtt    4920
cttcctgata gataaaatta atgcctttaa tcaggacatc actgctctca tgcaaggaga    4980
ggaaactgta ggggaggaag acattcggct gtttaccaga ctccgacacg agttccacaa    5040
atggagtaca ataattgaaa acaatttca agaaggccat aaaattttga gtagaaaat     5100 ccagaaattt gaaaatcagt atcgtggtag agagctgcca ggctttgtga attacaggac    5160
atttgagaca atcgtgaaac agcaaatcaa ggcactggaa gagccggctg tggatatgct    5220
acacaccgtg acggatatgg tccggcttgc tttcacagat gtttcgataa aaaatttga     5280
```

-continued

```
agagtttttt aacctccaca gaaccgccaa gtccaaaatt gaagacatta gagcagaaca    5340
agagagagaa ggtgagaagc tgatccgcct ccacttccag atggaacaga ttgtctactg    5400
ccaggaccag gtatacaggg gtgcattgca gaaggtcaga gagaaggagc tggaagaaga    5460
aaagaagaag aaatcctggg attttggggc tttccaatcc agctcggcaa cagactcttc    5520
catggaggag atctttcagc acctgatggc ctatcaccag gaggccagca agcgcatctc    5580
cagccacatc cctttgatca tccagttctt catgctccag acgtacggcc agcagcttca    5640
gaaggccatg ctgcagctcc tgcaggacaa ggacacctac agctggctcc tgaaggagcg    5700
gagcgacacc agcgacaagc ggaagttcct gaaggagcgg cttgcacggc tgacgcaggc    5760
tcggcgccgg cttgcccagt tccccggtta ggaattctgc agatatccag cacagtggcg    5820
gccgctcgag tctagagggc ccgtttaaac ccgctgatca gcctcgactg tgccttctag    5880
ttgccagcca tctgttgttt gcccctcccc cgtgccttcc ttgaccctgg aaggtgccac    5940
tcccactgtc ctttcctaat aaaatgagga aattgcatcg cattgtctga gtaggtgtca    6000
ttctattctg gggggtgggg tggggcagga cagcaagggg gaggattggg aagacaatag    6060
caggcatgct ggggatgcgg tgggctctat ggcttctgag gcggaaagaa ccagctgggg    6120
ctctaggggg tatccccacg cgccctgtag cggcgcatta gcgcggcgg gtgtggtggt    6180 tacgcgcagc gtgaccgcta cacttgccag cgccctagcg cccgctcctt tcgctttctt    6240
cccttccttt ctcgccacgt tcgccggctt tccccgtcaa gctctaaatc ggggctccc    6300 tttagggttc cgatttagtg ctttacggca cctcgacccc aaaaaacttg attagggtga    6360
tggttcacgt agtgggccat cgccctgata gacggttttt cgccctttga cgttggagtc    6420
cacgttcttt aatagtggac tcttgttcca aactggaaca acactcaacc ctatctcggt    6480
ctattctttt gatttataag ggattttgcc gatttcggcc tattggttaa aaaatgagct    6540
gatttaacaa aaatttaacg cgaattaatt ctgtggaatg tgtgtcagtt agggtgtgga    6600
aagtccccag gctccccagc aggcagaagt atgcaaagca tgcatctcaa ttagtcagca    6660
accaggtgtg gaaagtcccc aggctcccca gcaggcagaa gtatgcaaag catgcatctc    6720
aattagtcag caaccatagt cccgccccta actccgccca tcccgcccct aactccgccc    6780
agttccgccc attctccgcc ccatggctga ctaattttt ttatttatgc agaggccgag    6840
gccgcctctg cctctgagct attccagaag tagtgaggag gcttttttgg aggcctaggc    6900
ttttgcaaaa agctc                                                    6915
```

<210> SEQ ID NO 2
<211> LENGTH: 30
<212> TYPE: DNA
<213> ORGANISM: Artificial sequence
<220> FEATURE:
<223> OTHER INFORMATION: Synthetic primer

<400> SEQUENCE: 2
cgcaagctta tgaaagcgat cttaatccca                                    30

<210> SEQ ID NO 3
<211> LENGTH: 31
<212> TYPE: DNA
<213> ORGANISM: Artificial sequence
<220> FEATURE:
<223> OTHER INFORMATION: Synthetic primer

<400> SEQUENCE: 3
cacgaattct tacaaactgc acgccggtat g                                  31

<210> SEQ ID NO 4
<211> LENGTH: 28
<212> TYPE: DNA
<213> ORGANISM: Artificial sequence
<220> FEATURE:
<223> OTHER INFORMATION: Synthetic primer

<400> SEQUENCE: 4
agcaagctta tggttgtttc cgaagtgg                                    28

<210> SEQ ID NO 5
<211> LENGTH: 28
<212> TYPE: DNA
<213> ORGANISM: Artificial sequence
<220> FEATURE:
<223> OTHER INFORMATION: Synthetic primer

<400> SEQUENCE: 5
tatgaattcc taaccgggga actgggca                                    28

<210> SEQ ID NO 6
<211> LENGTH: 25
<212> TYPE: DNA
<213> ORGANISM: Artificial sequence
<220> FEATURE:
<223> OTHER INFORMATION: Synthetic primer

<400> SEQUENCE: 6
atctgcttag ggttaggcgt tttgc                                       25

<210> SEQ ID NO 7
<211> LENGTH: 29
<212> TYPE: DNA
<213> ORGANISM: Artificial sequence
<220> FEATURE:
<223> OTHER INFORMATION: Synthetic primer

<400> SEQUENCE: 7
ataacgcgtt tctttccgcc tcagaagcc                                   29

<210> SEQ ID NO 8
<211> LENGTH: 20
<212> TYPE: DNA
<213> ORGANISM: Artificial sequence
<220> FEATURE:
<223> OTHER INFORMATION: Synthetic primer

<400> SEQUENCE: 8
cgtgagaaac aggacgaaag                                             20

<210> SEQ ID NO 9
<211> LENGTH: 20
<212> TYPE: DNA
<213> ORGANISM: Artificial sequence
<220> FEATURE:
<223> OTHER INFORMATION: Synthetic primer

<400> SEQUENCE: 9
gccgagattt gccagattag                                             20

<210> SEQ ID NO 10
<211> LENGTH: 19
<212> TYPE: DNA
<213> ORGANISM: Artificial sequence
<220> FEATURE:
<223> OTHER INFORMATION: Synthetic primer

```
<400> SEQUENCE: 10
gcatcccacc ctctattac                                                   19

<210> SEQ ID NO 11
<211> LENGTH: 19
<212> TYPE: DNA
<213> ORGANISM: Artificial sequence
<220> FEATURE:
<223> OTHER INFORMATION: Synthetic primer

<400> SEQUENCE: 11
ccttgcctct ccacttatc                                                   19

<210> SEQ ID NO 12
<211> LENGTH: 20
<212> TYPE: DNA
<213> ORGANISM: Artificial sequence
<220> FEATURE:
<223> OTHER INFORMATION: Synthetic primer

<400> SEQUENCE: 12
tacacagcca ctcagaagac                                                  20

<210> SEQ ID NO 13
<211> LENGTH: 20
<212> TYPE: DNA
<213> ORGANISM: Artificial sequence
<220> FEATURE:
<223> OTHER INFORMATION: Synthetic primer

<400> SEQUENCE: 13
tttcacagcc tccgtgatag                                                  20
```